United States Patent [19]

Shaposka et al.

[11] Patent Number: 4,933,036

[45] Date of Patent: Jun. 12, 1990

[54] TECHNIQUES FOR WELDING THERMOPLASTIC TUBES

[75] Inventors: John B. Shaposka; Dudley W. C. Spencer, both of Wilmington, Del.

[73] Assignee: Denco, Inc., Wilmington, Del.

[21] Appl. No.: 393,687

[22] Filed: Aug. 16, 1989

Related U.S. Application Data

[60] Continuation-in-part of Ser. No. 312,027, Feb. 17, 1989, which is a division of Ser. No. 195,772, May 19, 1988, Pat. No. 4,832,773, which is a division of Ser. No. 99,714, Sep. 22, 1987, Pat. No. 4,770,735.

[51] Int. Cl.⁵ .................... B29C 65/18; B29C 65/20
[52] U.S. Cl. ..................... 156/158; 156/159; 156/273.3; 156/304.2; 156/304.5; 156/304.6; 156/309.9; 156/503; 156/507
[58] Field of Search ............ 156/158, 159, 304.2, 156/304.5, 304.6, 503, 507, 499, 309.9, 272.2, 273.3, 380.9; 604/905

[56] References Cited

U.S. PATENT DOCUMENTS

| | | | |
|---|---|---|---|
| 4,263,084 | 4/1981 | Takala | 156/158 |
| 4,507,119 | 3/1985 | Spencer | 156/304.2 |
| 4,737,214 | 4/1988 | Leurink et al. | 156/158 |
| 4,753,697 | 6/1988 | Shaposka et al. | 156/158 |
| 4,793,880 | 12/1988 | Shaposka et al. | 156/499 |

*Primary Examiner*—Michael Wityshyn
*Attorney, Agent, or Firm*—Connolly & Hutz

[57] ABSTRACT

Two thermoplastic tubes are welded together by pre-cutting the tubes to create two ends which are axially aligned when placed in a holding device. A wafer is inserted in the space between the cut ends and the wafer is heated to melt the cut ends while the cut ends are in a non-flattened condition. After the wafer is removed the melted cut ends are pressed against each other to weld the cut ends together.

3 Claims, 1 Drawing Sheet

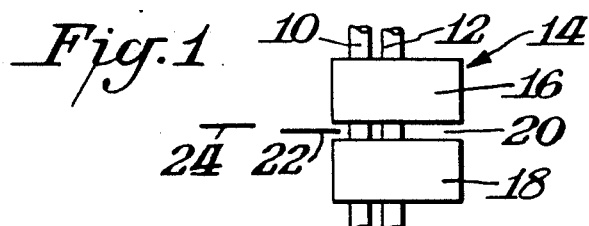
Fig. 1.
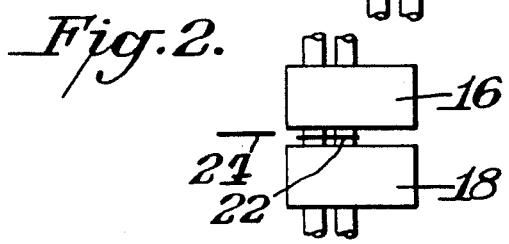
Fig. 2.
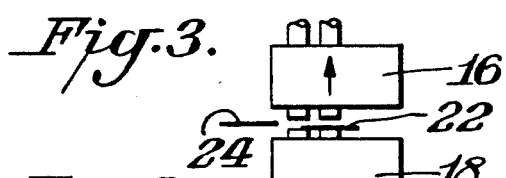
Fig. 3.
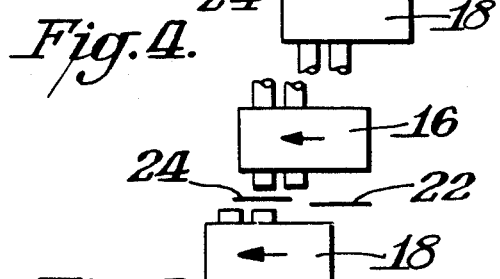
Fig. 4.
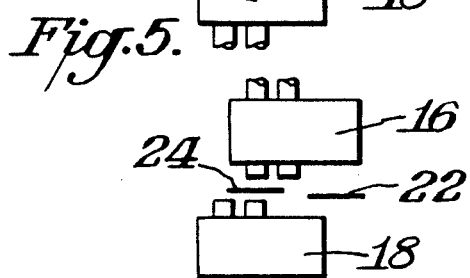
Fig. 5.
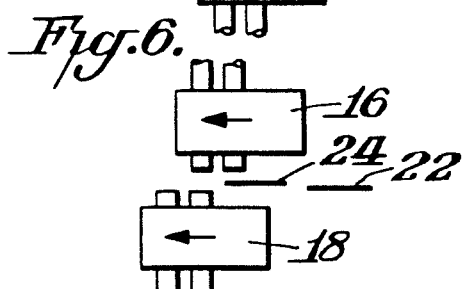
Fig. 6.
Fig. 7.
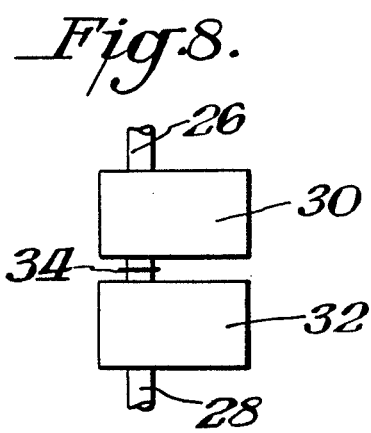
Fig. 8.
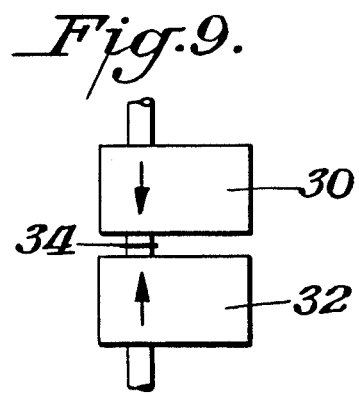
Fig. 9.
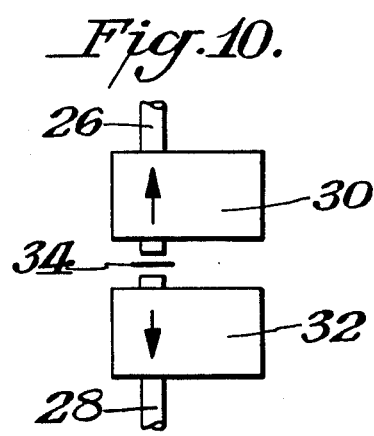
Fig. 10.
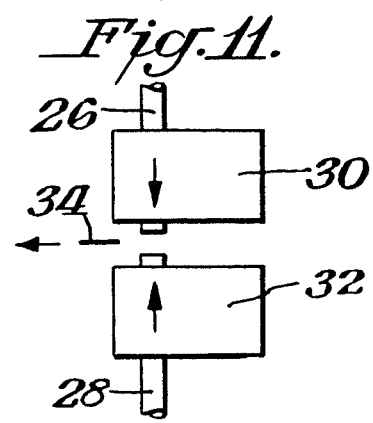
Fig. 11.

TECHNIQUES FOR WELDING THERMOPLASTIC TUBES

This application is a continuation in part of application Ser. No. 312,027 filed Feb. 17, 1989, which, in turn is a division of application Ser. No. 195,772, filed May 19, 1988, which, in turn is a division of application Ser. No. 99,714, filed Sept. 22, 1987, now U.S. Pat. No. 4,770,735, issued Sept. 13, 1988.

BACKGROUND OF INVENTION

This invention relates to improvements in the welding of thermoplastic tubes. Various techniques are known for such welding operations. Our U.S. Pat. No. 4,793,880, the details of which are incorporated herein by reference thereto, discusses prior techniques as well as the particular techniques which are the subject of that invention. A common use of such techniques is in dialysis when it is necessary to provide a patient with a fresh supply of liquid dialysate. Under such circumstances the tube containing the old dialysate which leads from the patient to the supply is severed. The same apparatus severs a tube leading from the new supply. The conventional techniques involve realigning the cut tubes so that the tube section from the new supply becomes aligned with the tube section from the patient. These aligned tube sections are then welded together to provide the patient with fresh dialysate.

The main emphasis in the techniques used heretofore have been concerned with the welding of fluid-filled tubes. With such techniques means had to be provided to flatten or seal each tube at two spaced locations so that a cutting device, usually a heated wafer, may cut through the tube between the two spaced locations.

The conventional approaches taken heretofore have also been generally confined to cutting through parallel tubes and then realigning the tube so as to form a single welded tube.

SUMMARY OF INVENTION

An object of this invention is to provide a method of welding thermoplastic tubes which are severed and welded while in their dry or fluid containing undistorted condition.

In accordance with one aspect of this invention a pair of round tubes are mounted in a holding device and are maintained in their round condition while the welding step takes place. In one embodiment of this invention, the tubes are mounted in a parallel relation during the severing step and then realigned for the welding step. In an alternative embodiment the tubes are pre-cut and then aligned to eliminate the need for a shifting or realignment step.

THE DRAWINGS

FIGS. 1-7 are plan views schematically illustrating the sequence of steps in accordance with one practice of this invention; and FIGS. 8-11 are plan views schematically illustrating the sequence of steps in accordance with a further practice of this invention.

DETAILED DESCRIPTION

FIGS. 1-7 illustrate a practice of this invention which is remarkably simpler than the conventional practice dealing with the welding of fluid filled tubes since the practice of FIGS. 1-7 could be used with dry tubes. As previously indicated the prior art has concentrated its efforts on the welding of fluid filled thermoplastic tubes such as used in dialysis. There are, however, many circumstances ignored by the prior art where it is desirable to weld thermoplastic tubes which do not contain fluid, but rather are in a dry condition. Such circumstances could include laboratory or test work as well as hospital pharmacy routines or methods wherein fluid is supplied only periodically. FIGS. 1-7 schematically illustrate the principles upon which this aspect of the invention is based. It is to be understood that once given the teachings of this invention those skilled in the art could use any suitable equipment for carrying out the invention. Our U.S. Pat. No. 4,793,880, for example, describes suitable equipment which could be modified to eliminate the clamping steps and otherwise be used in the practice of this invention. Accordingly, the details of that application are incorporated herein by reference thereto, rather than describing those details except as is necessary herein for an understanding of this invention.

As shown in FIG. 1 a pair of tubes 10, 12 made of thermoplastic material such as conventionally known in the prior art is mounted in parallel relation in a holding device 14 which includes a first clamp unit 16 and a second clamp unit 18 spaced from each other to form a gap 20. Although units 16 and 18 are referred to as clamp units, the only clamping that is necessary is to hold the tubes in place without flattening the tubes which differs from the prior art approach. During this loading step wafers 22, 24 are heated to their intended temperatures. Wafer 22 is a cutting wafer and is heated, for example, to ambient to about 500° F. and preferably to 350° F. Wafer 22 is preferably provided with a non-stick surface. Wafer 24 is made, for example, of nichrome and is heated to a temperature between 400-2000° F. and preferably 500-1200° F. since it functions in the welding step. Such wafers are known in the art.

FIG. 2 illustrates the severing step in which there is relative movement between the holding device 14 and wafer 22 so that warm wafer 22 passes into gap 20 to cut through tubes 10, 12.

FIG. 3 shows the sequence of operation wherein clamping unit 16 is moved away from clamping unit 18.

FIG. 4 illustrates the realigning step wherein clamping unit 16 is shifted as indicated to that a tube section from tube 10 in clamping unit 16 becomes aligned with a tube section from clamping unit 18. In this step warm wafer 22 is no longer between the cut tubes; rather hot wafer 24 is located between the aligned tube sections.

FIG. 5 illustrates the step wherein there is a pause to allow radiant heat from hot wafer 24 to melt and simultaneously sterilize the aligned tube ends.

FIG. 6 illustrates the step wherein hot wafer 24 is moved away from the aligned tube ends.

FIG. 7 illustrates the final sequence wherein clamping unit 18 is shifted to push the heated aligned tube ends together and effect the weld.

The advantages of the method of FIGS. 1-7 is that it provides a simplified technique for joining round dry tubes.

FIGS. 8-11 show a variation of the method of FIGS. 1-7. As indicated therein tube 26 and tube 28 are pre-cut so that their tube ends are reasonably squared. FIG. 8 illustrates the initial step where the pre-cut tubes 26, 28 are mounted in a pair of clamping units 30, 32 similar to units 16, 18 except that units 30, 32 need accommodate only one tube rather than a pair of tubes. As shown in FIG. 8 tube ends 26, 28 are pressed against a cold wafer 34.

FIG. 9 illustrates the next step of operation wherein the wafer 34 is turned on or heated and the tube ends 26, 28 are pressed into contact with wafer 34 by the shifting of clamping units 30, 32. During this step the surface of the tube ends is flattened to assure proper contact during the later welding step. The presence of the non-heated tubes holds down the wafer temperature. The wafer itself could be provided with a built-in temperature control.

FIG. 10 illustrates the next step wherein clamping units 30, 32 are moved away from each other to pull the tubes out of contact with and away from wafer 34. This allows the wafer temperature to rise and radiantly melt the exposed tube ends.

FIGS. 11 shows the next step wherein wafer 34 is moved away from the tube ends. Clamping units 30, 32 are then moved toward each other to press the tubes together and make the weld.

The practice of FIGS. 8–11 thus includes all of the advantages of the practice of FIGS. 1–7 but is even more simplified because it eliminates the shifting step. The wafer temperatures would be the same as in the practice of FIGS. 1–7.

The practice of FIGS. 8–11 has the advantage of eliminating the need for shifting to place the tube ends in alignment. The feature of the invention which uses a cold wafer for severing and a non-contacting hotter wafer to melt the tube ends provides the advantage of no consumables, thus permitting the use of permanent wafers. Although the invention has been described as being used with dry tubes and with a high temperature radiant source, the tube interior need not be dry. In fact, the tubes can be liquid filled since it has been found that after severing the liquid filled tubes, the liquid recedes slightly to permit a strong weld.

What is claimed is:

1. In a method of welding two thermoplastic tubes which are cut into sections with a cut end of one tube being aligned with a cut end of another tube and with the aligned cut ends being mounted in a holding device and being heated and then pressed together to become welded, the improvement comprising cutting the tubes before the tubes are mounted in the holding device, mounting the cut ends of the tubes in the holding device with the cut ends aligned, pressing the aligned cut ends against a cold wafer, heating the wafer to flatten the contacting surfaces of the cut ends, manipulating the holding device to withdraw the cut ends out of contact with the wafer, heating the wafer to radiantly melt the cut ends, withdrawing the wafer out of the path of movement of the cut ends, and pressing the melted cut ends into contact with each other to weld the cut ends together.

2. In the method of claim 1 wherein the cut ends are welded together while being of generally round cross section and in a dry condition without fluid in the tubes.

3. In the method of claim 1 wherein the cut ends are welded together while being of generally round cross section and fluid is in the tubes.

* * * * *